United States Patent
Hägel et al.

(10) Patent No.: US 7,214,812 B2
(45) Date of Patent: May 8, 2007

(54) STABILIZED PEROXYDICARBONATE PREPARATION

(75) Inventors: Eberhard Hägel, Icking (DE); Martin Kunz, Egling-Dettenhausen (DE); Werner Zeiss, Eurasburg (DE)

(73) Assignee: Peroxid-Chemie GmbH & Co. KG, Pullach (DE)

( * ) Notice: Subject to any disclaimer, the term of this patent is extended or adjusted under 35 U.S.C. 154(b) by 587 days.

(21) Appl. No.: 10/481,496

(22) PCT Filed: Jun. 26, 2002

(86) PCT No.: PCT/EP02/07072

§ 371 (c)(1),
(2), (4) Date: Dec. 19, 2003

(87) PCT Pub. No.: WO03/002527

PCT Pub. Date: Jan. 9, 2003

(65) Prior Publication Data

US 2004/0162438 A1 Aug. 19, 2004

(30) Foreign Application Priority Data

Jun. 28, 2001 (DE) ................. 101 31 147

(51) Int. Cl.
*C07C 409/00* (2006.01)
(52) U.S. Cl. ..................................... 558/261; 558/264
(58) Field of Classification Search ................ 558/260, 558/261, 264

See application file for complete search history.

(56) References Cited

U.S. PATENT DOCUMENTS

| | | | |
|---|---|---|---|
| 5,155,192 A * | 10/1992 | Boelema et al. ............ 526/228 |
| 5,548,046 A | 8/1996 | Sanchez | |
| 5,654,464 A * | 8/1997 | Abma et al. ................. 558/261 |
| 6,399,728 B1 | 6/2002 | Myers et al. | |
| 6,410,005 B1* | 6/2002 | Galleguillos et al. .... 424/70.16 |
| 6,893,584 B2* | 5/2005 | Bock et al. ............ 252/186.26 |

FOREIGN PATENT DOCUMENTS

| | | |
|---|---|---|
| EP | 0 810213 A | 12/1997 |
| EP | 0 853 082 A | 7/1998 |

\* cited by examiner

*Primary Examiner*—Golam M. M. Shameem
(74) *Attorney, Agent, or Firm*—Fulbright & Jaworski L.L.P

(57) ABSTRACT

The invention relates to a stabilized peroxydicarbonate preparation and its use in the polymerization or copolymerization of ethylenically unsaturated compounds.

7 Claims, No Drawings

STABILIZED PEROXYDICARBONATE PREPARATION

The invention relates to a stabilized peroxydicarbonate preparation and its use in the polymerization or copolymerization of ethylenically unsaturated compounds.

Peroxydicarbonates have the formula RO—CO—O—O—CO—OR, where R are organic radicals, generally alkyl, alkylene and aryl radicals. They are particularly useful for the initiation of polymerization reactions, since they are decomposed thermally to give free radicals even at relatively low temperatures. These peroxydicarbonates are preferably used for the polymerization of vinyl halides, in particular vinyl chloride, and can be used in an aqueous medium, for example as an emulsion, in solution or in suspension polymerization. However, their low decomposition temperature which is advantageous for use in polymerizations presents problems in storage, in transport and in handling.

The addition of stabilizing substances which improve the storage life and ease of handling is known. In practice, compositions comprising the peroxide and the stabilizer compound have been proposed for this purpose, but in practice these require temperatures of not more than −20° C. to be maintained.

Stabilizer compounds used in such compositions are phenolic antioxidants (U.S. Pat. No. 4,552,682), hydroperoxides (U.S. Pat. No. 5,155,192), unsaturated nitriles or 1,3-alkenynes (U.S. Pat. No. 5,541,151), β-dicarbonyl compounds (U.S. Pat. No. 5,714,626), phosphomolybdic acids (U.S. Pat. No. 5,719,304) or oximes (U.S. Pat. No. 5,892,090). However, these stabilized compositions which have been developed over a period of more than 15 years still leave something to be desired, in particular with regard to stabilization without diluents and conventional stabilizers and to the low temperatures which have to be maintained during storage. In addition, some of the known stabilizing additives are toxic or have an adverse effect on the color stability of the polymer prepared using them.

It is therefore an object of the invention to provide a stabilized peroxydicarbonate preparation which is storage-stable even at temperatures above −20° C. and even when the peroxide is not present in dissolved form but as pure product.

This object is achieved according to the invention by a stabilized peroxydicarbonate preparation which is characterized in that it consists essentially of a peroxydicarbonate and at least one alpha-unsaturated ketone of the formula (I)

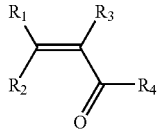

where
$R_1$ is H, alkyl, alkenyl or aryl,
$R_2$ is H, alkyl or aryl,
$R_3$ is H or alkyl,
$R_4$ is H, OH or $OR_5$ and
$R_5$ is alkyl or aryl or $R_1$ and $R_3$ together form a cycloalkenyl or oxacycloalkenyl radical.

The α-unsaturated ketones present as stabilizers in the preparation of the invention surprisingly make it possible to increase the SADTs (self-accelerating decomposition temperatures) according to the definition of the United Nations of the peroxydicarbonate preparations to temperatures above 0° C. and even make it possible to achieve SADTs for the composition which can be +10° C. or above.

The alkyl or/and alkenyl groups preferably have from 1 to 6 or from 2 to 6 carbon atoms. In a particularly preferred compound of the formula I, $R_1$ is a propenyl radical, $R_2$ and $R_3$ are each a hydrogen atom and $R_4$ is an OH group or an O-alkyl radical. Even greater preference is given to sorbic acid and its methyl and ethyl esters.

In a further preferred embodiment of the invention, the compound of the formula I has a phenyl radical as $R_1$ and a hydrogen atom as $R_2$ and as $R_3$. Among these compounds, particular preference is given to cinnamic acid and its ethyl and methyl esters.

In yet another preferred composition, the compound of the formula I contains a 5-membered oxacycloalkenyl ring formed by $R_1$ and $R_3$ together with the double bond. In this embodiment of the invention, particular preference is given to furan-2-carboxylic acid and its methyl and ethyl esters.

Peroxydicarbonates which can be used in the composition of the invention are compounds in which R is in each case an aliphatic, cycloaliphatic or aromatic group having up to 18 carbon atoms, preferably from 2 to 8 carbon atoms. The aliphatic groups can be straight-chain or branched alkyl or alkenyl radicals, cycloalkyl radicals or aromatic groups. Examples of suitable groups R are methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, t-butylcyclohexyl, t-amylcyclohexylbenzyl, phenylethyl, phenylbutyl and the corresponding known halogen- or/and nitro-substituted radicals.

Preferred peroxydicarbonates are selected from the group consisting of diethyl peroxydicarbonate, di-n-butyl peroxydicarbonate, diisobutyl peroxydicarbonate, di-sec-butyl peroxydicarbonate, di-2-ethyl-hexyl peroxydicarbonate, di-n-propyl peroxydicarbonate and diisopropyl peroxydicarbonate. Particular preference is given to using ethylhexyl peroxydicarbonate in the composition of the invention.

The components of the composition of the invention are known and can be obtained by methods which have been described.

The preparations of the invention are preferably free of significant amounts of solvent and can be prepared by simple mixing of the constituents. For this reason, preference is given to liquid peroxydicarbonates in which the compound of the formula I can be dissolved directly. However, it is also possible to use diluted peroxydicarbonates which are then mixed with solutions of the compound of the formula I to prepare the stabilized composition. Possible solvents are the solvents customarily used for peroxydicarbonates, e.g. phthalic esters and hydrocarbons. However, if the preparations are to be used as polymerization initiators, solvents are generally less desirable and are therefore not preferred.

As mentioned above, the preparations of the invention have, in particular, significantly increased SADTs and therefore considerably reduce the problems associated with storage and transport of these peroxides. The following examples illustrate this. The determination of the SADTs was carried out in accordance with the Recommendations on the Transport of Dangerous Goods, United Nations, 2nd edition, 1995, Part II, pp. 286–287.

EXAMPLES 1 TO 6

1) 1% by weight of ethyl sorbate is dissolved in technical-grade ethylhexyl peroxydicarbonate (purity: 99.2%) and this solution is subjected to the SADT test at +5° C. The solution remains stable for 15 days, i.e. the SADT is >5° C.
2) 2% by weight of ethyl sorbate is dissolved in technical-grade ethylhexyl peroxydicarbonate and this solution is subjected to the SADT test at +10° C. Decomposition occurs after 13 days, i.e. the SADT is +10° C.
3) 1% by weight of methyl furan-2-carboxylate is dissolved in technical-grade ethylhexyl peroxydicarbonate and this solution is subjected to the SADT test at +5° C. The solution is stable for 15 days, i.e. the SADT is >5° C.
4) 2% by weight of methyl furan-2-carboxylate is dissolved in technical-grade ethylhexyl peroxydicarbonate and this solution is subjected to the SADT test at +10° C. The solution remains stable, i.e. the SADT is >10° C.
5) 1.5% by weight of ethyl cinnamate is dissolved in technical-grade ethylhexyl peroxydicarbonate and this solution is subjected to the SADT test at +5° C. The solution remains stable. In the SADT test at +10° C., decomposition occurs after 6 days, i.e. the SADT is +10° C.
6) (Comparison) Technical-grade ethylhexyl peroxydicarbonate (99.2%) was subjected to the SADT test. Decomposition occurs at 0° C., i.e. the SADT is 0° C., and the storage and transport temperature has to be −20° C.

The invention claimed is:

1. A stabilized peroxydicarbonate composition comprising a peroxydicarbonate and at least one alpha-unsaturated ketone of the formula (I)

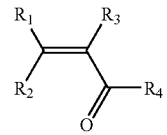

wherein
$R_1$ is H, alkyl, alkenyl or aryl,
$R_2$ is H, alkyl or aryl,
$R_3$ is H or alkyl,
$R_4$ is H, OH or $OR_5$ and
$R_5$ is alkyl or aryl or $R_1$ and $R_3$ together form a cycloalkenyl or oxacycloalkenyl radical.

2. A composition as claimed in claim 1, wherein at least one of the alkyl and alkenyl groups have up to 6 carbon atoms.

3. A composition as claimed in claim 2, wherein $R_1$ is a propenyl radical, $R_2$ and $R_3$ are each a hydrogen atom and $R_4$ is an OH group or an O-alkyl radical.

4. A composition as claimed in claim 2, wherein $R_1$ is a phenyl radical, $R_2$ and $R_3$ are each a hydrogen atom.

5. A composition as claimed in claim 1, wherein $R_1$ and $R_3$ together form a 5-membered oxacycloalkenyl ring.

6. A composition as claimed in claim 1, wherein the peroxydicarbonate is selected from the group consisting of diethyl peroxydicarbonate, di-n-butyl peroxydicarbonate, diisobutyl peroxydicarbonate, di-sec-butyl peroxy-dicarbonate, di-2-ethylhexyl peroxydicarbonate, di-n-propyl peroxydicarbonate and diisopropyl peroxydicarbonate.

7. A composition as claimed in claim 6, comprising comprises di-2-ethylhexyl peroxy-dicarbonate.

* * * * *